*(12)* United States Patent
Bertling

(10) Patent No.: US 7,303,884 B1
(45) Date of Patent: Dec. 4, 2007

(54) METHOD FOR INDIRECTLY DETERMINING THE BLOOD-CLOTTING STATUS

(75) Inventor: Wolf Bertling, Erlangen (DE)

(73) Assignee: november Aktiengesellschaft Gesellschaft für Molekulare Medizin, Erlangen (DE)

( * ) Notice: Subject to any disclaimer, the term of this patent is extended or adjusted under 35 U.S.C. 154(b) by 747 days.

(21) Appl. No.: 10/049,574

(22) PCT Filed: Aug. 11, 2000

(86) PCT No.: PCT/DE00/02748

§ 371 (c)(1),
(2), (4) Date: Jul. 16, 2002

(87) PCT Pub. No.: WO01/13123

PCT Pub. Date: Feb. 22, 2001

(30) Foreign Application Priority Data

Aug. 14, 1999 (DE) .................................. 199 37 654
Aug. 31, 1999 (DE) .................................. 199 41 447

(51) Int. Cl.
*G01N 33/53* (2006.01)
(52) U.S. Cl. ..................... 435/7.1; 435/7.92; 435/7.93; 435/7.94; 436/501; 436/164; 436/172
(58) Field of Classification Search ................. 435/7.1, 435/7.92–7.95, 973, 975; 436/501, 518, 436/524, 164, 172, 808
See application file for complete search history.

(56) References Cited

U.S. PATENT DOCUMENTS

| 4,769,320 | A |   | 9/1988  | Furie et al.       |         |
|-----------|---|---|---------|--------------------|---------|
| 4,780,410 | A |   | 10/1988 | Matsuda et al.     |         |
| 5,252,712 | A |   | 10/1993 | Furie et al.       |         |
| 5,516,640 | A | * | 5/1996  | Watanabe et al.    | 435/7.4 |
| 5,843,666 | A | * | 12/1998 | Akhavan-Tafti et al. | 435/6 |
| 6,503,724 | B1 | * | 1/2003 | De Nora et al.     | 435/13  |

FOREIGN PATENT DOCUMENTS

DE          40 08 546 A1     9/1990

| JP | 05284994 A | 11/1993 |
|----|------------|---------|
| WO | WO 99/09058 | 2/1999 |
| WO | WO 00/58732 | 10/2000 |

OTHER PUBLICATIONS

Brown, Hematology: Sixth Edition, Principles and Procedures, 1993, p. 213.*
Taber's Cyclopedic Medical Dictionary, Edition 17, F.A. Davis Company, 1993, p. 1786.*
von Kries et al., "Des-gamma-carboxyprothrombin (PIVKA II) and plasma vitamin K1 in newborns and their mothers," *Thromb. Haemost.*, 1992, 68(4):383-387 (Abstract only).
Weinstock et al., "Comparison of Plasma Prothrombin and Factor VII and Urine Prothrombin F1 Concentrations in Patients on Long-Term Warfarin Therapy and Those in the Initial Phase," *Am. J. Hematol.*, 1998, 57:193-199.

* cited by examiner

*Primary Examiner*—Long V. Le
*Assistant Examiner*—Gary W. Counts
(74) *Attorney, Agent, or Firm*—Fish & Richardson P.C.

(57) ABSTRACT

The invention relates to a method for indirectly determining the blood-clotting status. The inventive method comprises the following steps: a) collecting body fluids which contain a protein that can be modified by a vitamin K-dependent γ-carboxylase, b) determining at least two concentrations selected from a group consisting of a first concentration C1 of carboxylated protein, a second concentration C3 of decarboxylated protein and an entire concentration C3 of carboxylated and decarboxylated protein, whereby the first concentration C1 is determined using a first antibody A1, the second concentration using a second antibody A2 and the third concentration C3 using a third antibody A3, c) generating a first quotient Q1 from the first C1 and second C2 concentration or generating a second quotient Q2 from the third C3 and first C1 concentration or generating a third quotient Q3 from the third C3 and second concentration C2, whereby a concentration C1, C2, C3 which has not been determined in step b) and which is required for generating the first Q1, the second Q2, or the third quotient Q3 is calculated according to the following relation: C3−C2=C1 and d) the first, second or third quotient Q1, Q2, Q3 are correlated with the blood-clotting status.

11 Claims, 3 Drawing Sheets

METHOD FOR INDIRECTLY DETERMINING THE BLOOD-CLOTTING STATUS

CROSS-REFERENCE TO RELATED APPLICATIONS

This application is a National Stage application under 35 U.S.C. § 371 and claims benefit under 35 U.S.C. § 119(a) of International Application No. PCT/DE00/02748 having an International Filing Date of Aug. 11, 2000, which claims benefit of DE 199 37 654.9 filed on Aug. 14, 1999 and DE 199 41 447.5 filed on Aug. 31, 1999.

The invention relates to a method for indirectly determining the blood clotting status. The blood clotting status can be determined indirectly by measuring the prothrombin concentration in human body fluids. Prothrombin is a protein which occurs chiefly in human blood plasma. This protein can be modified by a vitamin K-dependent γ-carboxylase. Prothrombin is partly responsible for blood clotting. It converts fibrinogen into fibrin.

The fibrinogen conversion induced by prothrombin takes place only when prothrombin is present in natural carboxylated form. The carboxylation is effected in the liver by a carboxylase with binding of the cofactor vitamin K. The carboxylase activity depends on the vitamin K concentration. If the carboxylase activity is reduced, an abnormal, noncarboxylated form of prothrombin which has no clotting activity is produced.

In healthy people, prothrombin is present in the natural, i.e. carboxylated, form. Vitamin K acts as cofactor in the carboxylation. In people who are ill, especially in people with liver damage, or on addition of anticoagulants, prothrombin also occurs in the abnormal form.

Carboxylated prothrombin brings about clotting only if $Ca^{2+}$ ions are bound beforehand. Only then is the carboxylated prothrombin able to bind to the membranes of blood platelets and bring about clotting. Only the carboxylated form of prothrombin is able to bind calcium. The blood clotting status can thus be inferred from the content of carboxylated prothrombin.

U.S. Pat. No. 4,769,320 discloses a method in which the content of carboxylated prothrombin is measured by use of antibodies in an immunoassay. The antibodies are specific for carboxylated prothrombin in the presence of calcium. They do not bind to decarboxylated prothrombin. A kit for determining the level of carboxylated prothrombin in a plasma sample is described and contains such an antibody.

U.S. Pat. No. 5,252,712 discloses a monoclonal antibody which is specific for noncarboxylated prothrombin. It is possible by use of this antibody in an immunoassay to measure the concentration of uncarboxylated prothrombin. This also makes it possible to gain information about the blood clotting status.

U.S. Pat. No. 4,780,410 discloses a sandwich immunoassay method for quantifying decarboxylated prothrombin. An immobilized monoclonal antibody directed against decarboxylated prothrombin is used in the method. Decarboxylated prothrombin binding thereto is detected by a second antibody directed against prothrombin. A kit for carrying out the method is also described.

Kornberg A. et al., *Circulation* 88 (1993), pages 454-460, disclose determination of the concentration of carboxylated prothrombin in a sample by use of a competitor. In this case, peroxidase-labeled prothrombin competes as competitor with the prothrombin in the sample for binding to an immobilized anti-prothrombin antibody. The peroxidase-labeled prothrombin bound to the anti-prothrombin antibody can be detected by an enzyme reaction. The size of the signal produced thereby is inversely proportional to the prothrombin concentration in the sample.

JP 05 284 994 A discloses three monoclonal antibodies. A first one binds specifically to human decarboxylated prothrombin, a second one binds specifically to human prothrombin, human thrombin and human decarboxylated prothrombin and a third one binds specifically to human decarboxylated prothrombin and human prothrombin.

The determination of decarboxylated prothrombin in blood by means of an ELISA using a monoclonal antibody is disclosed by von Kries, R. et al., *Thrombosis and Haemostatis* 68 (1992), pages 383-387.

The problem which arises in the prior art is that the sample material to be analyzed is not always analyzed immediately after the sample is taken. 1 to 2 days elapse on occasion through transport of the sample material. Most of the factors involved in blood clotting are highly sensitive and rapidly inactive. During this time, inter alia both carboxylated and noncarboxylated prothrombin in the sample is broken down. The consequence is falsification of the results of the blood clotting status.

It is an object of the invention to eliminate the disadvantages of the prior art. It is intended in particular to increase the accuracy of measuring the blood clotting status by determination of the prothrombin content. It is further intended to provide a kit which makes possible more accurate measurement of the blood clotting status.

According to the invention, a method for indirectly determining the blood clotting status having the following steps is provided:

a) removal of body fluid which contains a protein which can be modified by a vitamin K-dependent γ-carboxylase, b) measuring at least two concentrations selected from a group consisting of a first concentration of carboxylated protein, a second concentration of decarboxylated protein and a total concentration of carboxylated and decarboxylated protein, where the first concentration is measured using a first antibody, the second concentration is measured using a second antibody and the third concentration is measured using a third antibody, c) forming a first ratio from the first and second concentration or forming a second ratio from the third and first concentration or forming a third ratio from the third and second concentration, where a concentration which is necessary for forming the first, second or third ratio and is not measured in step b) is calculated in accordance with the following relation:

$$C3-C2=C1$$

and d) correlating the first, second or third ratio with the blood clotting status.

A protein which can be modified by a vitamin K-dependent γ-carboxylase means a protein which, depending on the blood clotting status, may be present in proportions both of the carboxylated and of the decarboxylated form. The protein may be a protein which can easily be obtained from a patient, e.g. a protein from the saliva. The protein may be a protein which is subject to the same percentage hypomodification as prothrombin. An antibody may be, for the purpose of the invention, an antibody, an antibody fragment or another substance with binding specificity for the carboxylated form, the decarboxylated form or both forms of the protein.

It is possible with the method of the invention to measure accurately the blood clotting status on the basis of the content of modifiable protein. Errors in the determination of the blood clotting status are minimized through taking account both of the content of carboxylated protein and of the content of decarboxy- lated protein and the relating of the two aforementioned protein contents.

In one embodiment of the invention, in step b) additionally at least a first competitor is used to measure the first concentration, a second competitor is used to measure the second concentration or a third competitor is used to measure the third concentration. The competitor is a substance which competes with the carboxylated protein, the decarboxylated protein or the carboxylated and decarboxylated protein for binding to one of the antibodies. The competitor may be the carboxylated or decarboxylated protein, in which case it is provided with a labeling substance. In place of the complete protein it is also possible to use a fragment of this protein as competitor.

It is preferred for at least one of the antibodies or at least one of the competitors to be conjugated to a labeling substance, in particular an enzyme, a fluorescent dye, a quencher, a gold particle, a latex particle, biotin, streptavidin or avidin. Any enzyme detectable by means of an enzymatic reaction can be used as enzyme. The labeling of the antibody with a gold particle permits the bound antibody to be detected by a plasmon resonance method.

In place of measuring the at least two concentrations as in step b) it is also possible for a combined signal correlating therewith to be generated and measured by using two antibodies selected from a group consisting of the first, the second and the third antibody and, where appropriate, at least one of the competitors, and be directly correlated with the blood clotting status. The combined signal is produced by different individual signals acting together. It corresponds to the first, second or third ratio. The formation of these ratios as in step c) is dispensed with. This makes it possible to carry out the method more quickly and simply. The combined signal may be a combined color, generated in particular by fluorescent dyes, a fluorescent signal elicited by the Förster effect or a reduction caused by the quencher in a fluorescent signal. The combined color may also be generated by two enzymes which each catalyze a specific color reaction. The Förster effect involves a radiationless energy transfer from an excited first fluorophore to a directly adjacent second fluorophore. The first fluorophore thus makes the transition to the ground state, while the second fluorophore is excited and fluoresces. In the method of the invention it is possible, for example, for the first and second antibodies to be conjugated with fluorophores which make the first effect possible. The binding of the first antibodies directly adjacent to the second antibodies can be established by means of a fluorescent signal elicited by the Förster effect. When there is a radiationless energy transfer from fluorophore to quencher the fluorescence is quenched. The total measurable fluorescent signal is thus reduced.

The body fluid may expediently be plasma, blood, saliva, urine or the like. All body fluids in which the modifiable protein is present in a content which makes measurement possible are suitable in principle.

According to one developmental feature of the invention, the measurement of the first, second and/or third concentration or of the combined signal takes place by an immunological method. The immunological method in this case may involve at least one of the antibodies being immobilized on a support, in particular a plastic, a magnetic particle, a latex particle, a gold particle, a test strip or a membrane. The plastic may be in the form of a test tube, a test strip, a plastic particle or a well of a microtiter plate.

The first, second and/or third concentration and/or the combined signal can be measured by means of a color reaction or fluorescence detection. This makes possible particularly rapid and simple measurement of the blood clotting status.

The protein which can be modified by a vitamin K-dependent γ-carboxylase is preferably one of the clotting factors which are referred to in the decarboxylated form as "proteins induced by vitamin K antagonism or absence" (PIVKA factors): prothrombin, factor VII, factor IX or factor X, or is nephrocalcin or osteocalcin. It is also possible to use for determining the blood clotting status other proteins which are carboxylated by a vitamin K-dependent carboxylase and can likewise be influenced by anticoagulants which can be administered orally. Nephrocalcin is, for example, detectable in urine. It is unnecessary to take any blood on use of this protein. This means a considerable alleviation for patients whose blood clotting status must be monitored continuously.

Also provided is a kit for carrying out the method of the invention, comprising at least two antibodies selected from a group consisting of a first antibody for immunological determination of a first concentra- tion of the carboxylated form of the protein, a second antibody for immunological determination of a second concentration of the decarboxylated form of the protein and a third antibody for immunological determination of a total concentration of carboxylated and decarboxylated protein.

The first, second and third antibody may be antibodies known in the prior art. Such antibodies are disclosed, for example, in U.S. Pat. No. 5,252,712 and U.S. Pat. No. 4,769,320, the contents of which are incorporated herein by reference.

The kit may additionally comprise at least a first competitor for measuring the first concentration, a second competitor for measuring the second concentration or a third competitor for measuring the third concen- tration. At least one of the antibodies or competitors present in the kit may be conjugated to a labeling substance, in particular an enzyme, a fluorescent dye, a quencher, a gold particle, a latex particle, biotin, streptavidin or avidin.

The first and the second antibody are preferably immobilized on a support. The support may be a plastic, a magnetic particle, a latex particle, a gold particle, a test strip or a membrane. If the support is a test strip, the first and the second antibody may each be absorbed on a separate field on the test strip. The kit preferably comprises a third antibody conjugated to a labeling substance, in particular an enzyme, a fluorescent dye, a quencher, a gold particle, a latex particle, biotin, streptavidin or avidin. This makes it possible to measure the respective content particularly simply, for example by means of a color reaction on the test strip.

In a further development of the invention, the third antibody is immobilized on the or another support, in particular a plastic, a magnetic particle, a latex particle, a gold particle, a test strip or a membrane. If the support is the or another test strip, the third antibody can be absorbed on a field of the test strip. The kit preferably comprises a first and second antibody in each case conjugated to a labeling substance, in particular an enzyme, a fluorescent dye or a quencher, where the labeling substances are selected so that they are able together to generate a combined signal, in particular a combined color, a fluorescent signal elicited by the Förster effect or a reduction caused by a quencher in a fluorescent signal. The combined signal corresponds to the first ratio.

The protein is preferably prothrombin, factor VII, factor IX, factor X, nephrocalcin or osteocalcin.

The method of the invention is explained hereinafter by means of the drawing.

Figure 1:
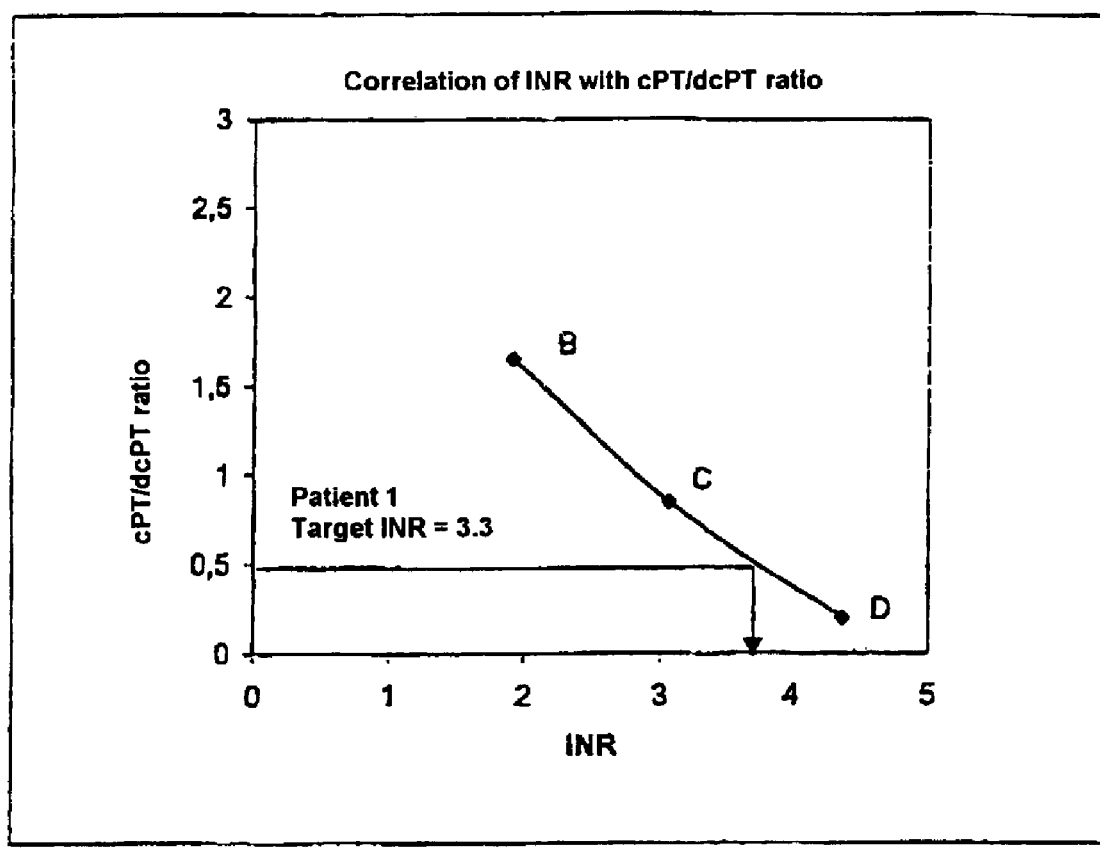
FIG. 1 shows the correlation of the blood clotting status with cPT/dcPT.

FIG. 1 is a plot of the ratio of the concentrations of carboxylated and decarboxylated prothrombin against the blood clotting status INR. The concentrations in this case are measured as OD values. The blood clotting status INR which results from a measured ratio of 0.5 is 3.8.

Figure 2:
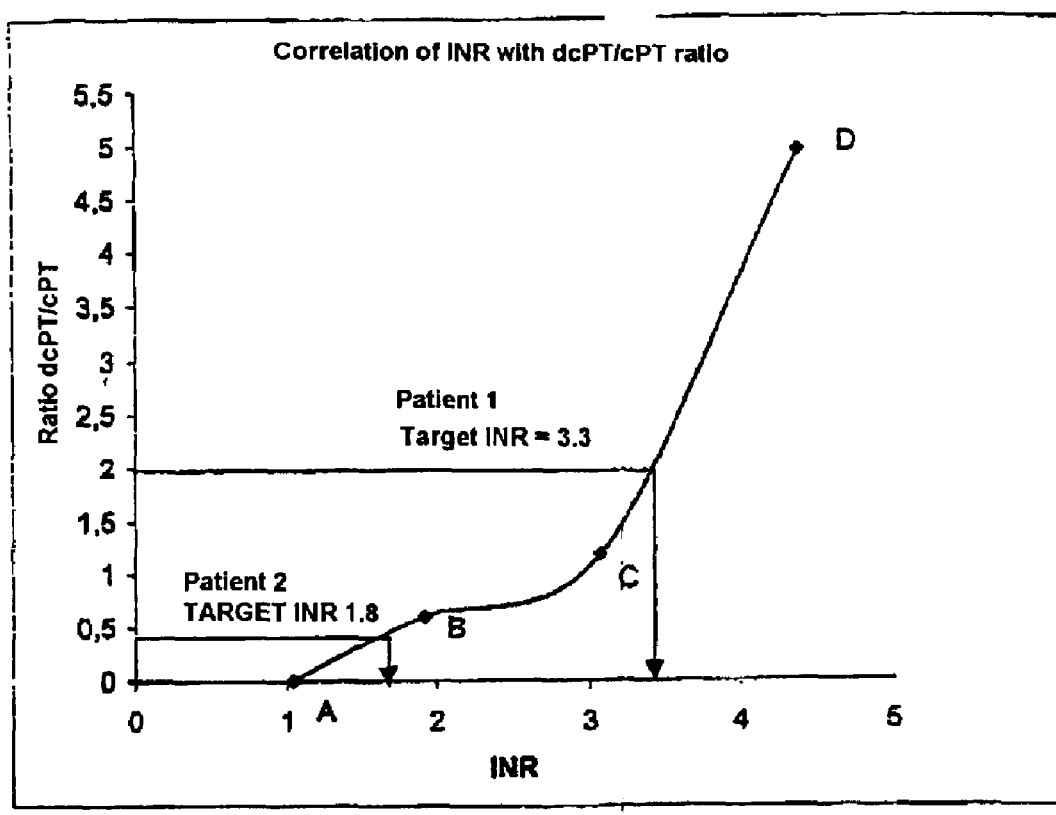
FIG. 2 shows the correlation of the blood clotting status with dcPT/cPT.

FIG. 2 is a plot of the ratio of the concentrations of decarboxylated and carboxylated prothrombin against the blood clotting status. It is evident that the ratio in this case correlates particularly well with the blood clotting status INR.

Figure 3:
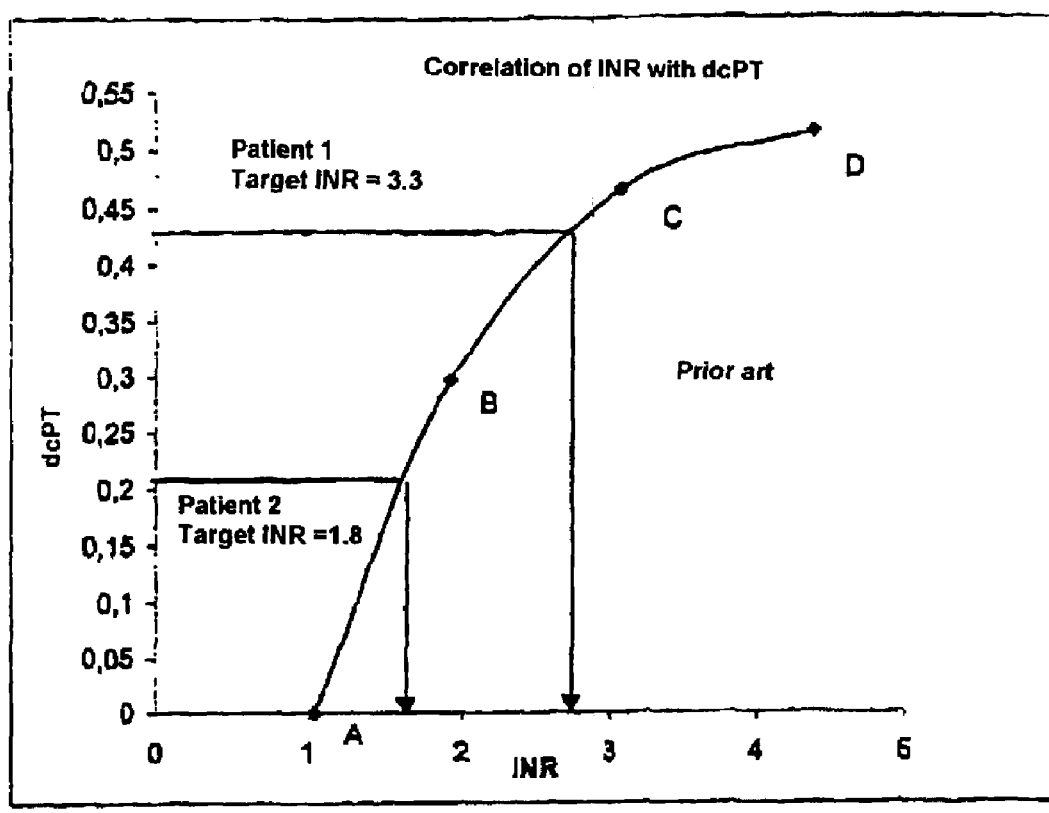
FIG. 3 shows the correlation of the blood clotting status with dcPT.

FIG. 3 shows the correlation known from the prior art of dcPT with the blood clotting status INR. This changes with increasing age of the samples.

Example 1

The so-called ELISA on a microtiter plate is particularly suitable for serial measurements.

a) Sample preparation:

The cavities of a microtiter plate (Maxisorb, NUNC) are each coated with 50 µl of an antibody (10 µg/ml in carbonate buffer) at 4° C. overnight. The cavities are washed three times with PBS. Nonspecific binding sites are saturated with 50 µl of 1% BSA in PBS per well at room temperature for 1 hour. The cavities are then washed three times with PBS/0.05% Tween 20.

The following samples are then loaded, each diluted 1:50 in PBS/0.1% BSA (50 µl/cavity):
calibration plasmas,
normal plasma,
patient's plasma and
prothrombin-deficient plasma (negative control).

The microtiter plate is incubated at room temperature for one hour. The cavities are then washed three times with PBS/0.05% Tween 20. 50 µl/cavity of rabbit anti-complete prothrombin (10 µg/ml) are added. The mirotiter plate is then incubated at room temperature for one hour. The cavities are then washed three times with PBS/0.05% Tween 20. 50 µl/cavity of goat anti-rabbit antibody, biotin-conjugated (Dionova, 1:20 000 in PBS/0.1% BSA) are added. The microtiter plate is incubated at room temperature for one hour. The cavities are then washed three times with PBS/0.05% Tween 20.

50 µl/cavity of streptavidin-peroxidase conjugate (Roche Diagnostics, 1:1000 in conjugate buffer) are added. The microtiter plate is incubated at room temperature for one hour. The cavities are then washed three times with PBS/0.05% Tween 20.

To carry out the development reaction, 50 µl/cavity of ABTS solution (Roche Diagnostics, 1 mg/ml) are added. The microtiter plate is incubated at room temperature for half an hour to one hour. The absorptions (OD values) are measured in an ELISA reader.

It is self-evident that the method can be considerably shortened if the anti-prothrombin antibody used for detecting bound prothrombin already has a labeling substance such as peroxidase or another enzyme. A further shortening of the method can be achieved by using a directly detectable labeling substance such as a fluorophore. No development reaction is necessary on use of such a labeling substance.

b) Evaluation:

The following are determined:
aa) the OD values of the complete prothrombin (cavities are coated with monoclonal anti-complete prothrombin antibodies),
bb) the OD values of the decarboxylated prothrombin (cavities are coated with monoclonal anti-decarboxyprothrombin antibodies) and
cc) the OD values of the carboxylated prothrombin (difference between the OD values of the complete prothrombin and the OD values of the decarboxylated prothrombin).

Then calibration plots are constructed from the measured OD values (see FIGS. 1-3: points A, B, C and D) of the calibration plasmas, and the INR of the patient's plasmas calculated.

It is self-evident that the clotting status can also be measured by measuring the corresponding concentrations of proteins other than prothrombin which can be modified by a vitamin K-dependent γ-carboxylase. Examples of such proteins are factor VII, factor IX, factor X, nephro-calcin or osteocalcin.

Example 2:

The cavities of a microtiter plate (Maxisorb, NUNC) are coated with in each case 50 µl of an antibody directed against carboxylated and decarboxylated prothrombin or of an antibody directed only against decarboxylated prothrombin (10 µg/ml in carbonate buffer) at 4° C. overnight. The cavities are washed three times with PBS. Nonspecific binding sites are saturated with 50 µl of 1% BSA in PBS per cavity at room temperature for one hour. The cavities are then washed three times with PBS/0.05% Tween 20.

Peroxidase-labeled decarboxylated prothrombin is pulled together with the following samples, each diluted 1:50 in PBS/0.1% BSA, in a final concentration of 30 µg/ml into the antibody-coated cavities of the microtiter plate (50 µl/cavity):
calibration plasmas,
normal plasma,
patient's plasma and
prothrombin-deficient plasma (negative control).

The microtiter plate is incubated at room temperature for one hour. The cavities are then washed three times with PBS/0.05% Tween 20. 50 µl/cavity of ABTS solution (Roche Diagnostics, 1 mg/ml) are added. The microtiter plate is incubated at room temperature for half an hour to one hour. The OD values in the cavities of the microtiter plate are measured in an ELISA reader. A higher OD value in a cavity means a lower concentration of prothrombin in the particular sample. The prothrombin concentration in the patient's plasma is measured by means of a calibration plot constructed using the calibration plasmas. Cavities coated with the antibody against carboxylated and decarboxylated prothrombin are used to determine the total concentration of carboxylated and decarboxylated prothrombin. Cavities coated with the antibody directed against decarboxylated prothrombin are used to determine the concentration of decarboxylated prothrombin. The ratio of the measured total concentrations of carboxylated and decarboxylated and the concentration of decarboxylated prothrombin is found. The clotting status can be measured from the resulting ratio on the basis of the ratios for the calibration plasmas.

The invention claimed is:

1. A method for indirectly determining blood clotting status INR (International Normalized Ratio) comprising the following steps:
  a) providing a sample of body fluid which contains a protein which can be modified by a vitamin K-dependent γ-carboxylase, wherein the body fluid is plasma, blood, saliva, or urine,
  b) measuring at least two concentrations selected from a group consisting of a first concentration (C1) of carboxylated protein, a second concentration (C2) of decarboxylated protein and a third concentration (C3) of total carboxylated and decarboxylated protein, where the first concentration (C1) is measured using a first antibody (A1), the second concentration is measured using a second antibody (A2) and the third concentration (C3) is measured using a third antibody (A3),
  c) obtaining a first ratio (R1) from the first (C1) and second concentration (C2) or forming a second ratio (R2) from the third (C3) and first concentration (C1) or forming a third ratio (R3) from the third (C3) and second concentration (C2),
  where a concentration (C1, C2, C3), which is necessary for forming the first (R1), second (R2) or third (R3) ratio, is not measured in step b) is calculated in accordance with the following relation:

$$C3-C2=C1$$

and
  d) correlating the first, second or third ratio (R1, R2, R3) with the blood clotting status.

2. The method as claimed in claim 1, where in step b) additionally at least a first competitor (K1) is used to measure the first concentration (C1), a second competitor (K2) is used to measure the second concentration (C2) or a third competitor (K3) is used to measure the third concentration (C3).

3. The method as claimed in claim 2, where at least one of the antibodies (A1, A2, A3) or at least one of the competitors (K1, K2, K3) is conjugated to a labeling substance.

4. The method as claimed in claim 2, where in place of measuring the at least two concentrations as in step b), a combined signal correlating therewith is generated and measured by using two antibodies selected from a group consisting of the first (A1), the second (A2) and the third antibody (A3) and, where appropriate, at least one of the competitors (K1, K2, K3), and is directly correlated with the blood clotting status.

5. The method as claimed in claim 4, where the combined signal is a combined color generated by fluorescent dyes, a fluorescent signal elicited by the Förster effect or a reduction caused by the quencher in a fluorescent signal.

6. The method as claimed in claim 1, where the measurement of the first (C1), second (C2) and/or third concentration (C3) or of the combined signal takes place by an immunological method.

7. The method as claimed in claim 6, where in the immunological method, at least one of the antibodies (A1, A2, A3) is immobilized on a support.

8. The method as claimed in claim 1, where the first (C1), second (C2) and/or third concentration (C3) and/or the combined signal is measured by means of a color reaction or fluorescence detection.

9. The method as claimed in claim 1, where the protein which can be modified by a vitamin K-dependent γ-carboxylase is prothrombin, factor VII, factor IX, factor X, nephrocalcin or osteocalcin.

10. The method of claim 3, wherein the labeling substance is selected from the group consisting of an enzyme, a fluorescent dye, a quencher, a gold particle, a latex particle, biotin, streptavidin, and avidin.

11. The method of claim 7, wherein the support is selected from the group consisting of a plastic, a magnetic particle, a latex particle, a gold particle, a test strip, and a membrane.

* * * * *